(12) United States Patent
Ries et al.

(10) Patent No.: US 8,515,556 B2
(45) Date of Patent: Aug. 20, 2013

(54) REINFORCED SILICONE INSULATION FOR IMPLANTABLE MEDICAL ELECTRICAL LEADS

(75) Inventors: Richard Dean Ries, Stillwater, MN (US); James M Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 116 days.

(21) Appl. No.: 12/915,854

(22) Filed: Oct. 29, 2010

(65) Prior Publication Data

US 2012/0109271 A1     May 3, 2012

(51) Int. Cl.
*A61N 1/00*     (2006.01)

(52) U.S. Cl.
USPC ........................................................ 607/115

(58) Field of Classification Search
USPC .......... 607/115, 116, 119, 122; 600/373–374
See application file for complete search history.

(56) References Cited

U.S. PATENT DOCUMENTS

| | | |
|---|---|---|
| 2006/0008606 A1 | 1/2006 | Horn et al. |
| 2006/0030835 A1 | 2/2006 | Sherman et al. |
| 2010/0016891 A1 | 1/2010 | Kennedy et al. |
| 2010/0063599 A1* | 3/2010 | Brunelle et al. ........... 623/23.72 |
| 2010/0228262 A1 | 9/2010 | Cully et al. |
| 2011/0218602 A1* | 9/2011 | Kampa et al. .................. 607/116 |

FOREIGN PATENT DOCUMENTS

| | | |
|---|---|---|
| WO | WO 96/03175 A1 | 2/1996 |
| WO | WO 2006/127763 A1 | 11/2006 |
| WO | 2009124762 A1 | 10/2009 |

OTHER PUBLICATIONS (PCT/US2011/058299) PCT Notification of Transmittal of the International Search Report and the Written Opinion of the International Searching Authority.

* cited by examiner

*Primary Examiner* — Niketa Patel
*Assistant Examiner* — Minh Duc Pham
(74) *Attorney, Agent, or Firm* — Reed A. Duthler

(57) ABSTRACT

An improvement to silicone insulation for implantable medical electrical leads includes a plurality of ultra high molecular weight polyethylene multi-filament fibers, wherein each of the plurality includes approximately 25 monofilaments and has a titer of approximately 25. The plurality of fibers are embedded within a wall of the insulation that has a thickness of no greater than approximately 0.008 inch. A first fiber of the plurality preferably extends helically, and a second fiber of the plurality preferably extends linearly such that the second crosses over or under and directly adjacent to the first at a plurality of points, which are spaced apart from one another along an overall length of the silicone insulation. The aforementioned wall thickness is maintained, since, at least at each crossing point of the first and second multi-filament fibers, a coincident cross-section of each of the fibers is compressed in the radial direction.

18 Claims, 3 Drawing Sheets

REINFORCED SILICONE INSULATION FOR IMPLANTABLE MEDICAL ELECTRICAL LEADS

TECHNICAL FIELD

The present disclosure pertains to implantable medical electrical leads and more particularly to the silicone insulation thereof.

BACKGROUND

A number of suitable silicone elastomer materials are available as insulation to provide electrical isolation for the conductors of implantable medical electrical leads, for example, which are employed for cardiac and neurological stimulation and sensing. In many types of implantable leads, the insulation is typically in the form of extruded tubing that has at least one lumen for the passage of electrical conductors therethrough. The insulation tubing is typically required to have a minimum wall thickness (which depends upon the properties of the selected type of silicone elastomer), in order to withstand degradation, for example, due to compressive and tensile loading applied at the time of implant, as well as at explant, and as exerted by the implant environment over the course of implantation, and/or due to abrasion within the implant environment. Some examples of commercially available silicone elastomers which have been, and/or are currently used for the insulation tubing of implantable medical electrical leads include MED-4755, Med-4770 and MED-4719, which are available from NuSil Technology LLC (Carpinteria, Calif.). Silicone elastomers such as these have demonstrated sufficient strength and long term stability/durability to provide the required electrical isolation, for a given wall thickness, when used as the primary insulation in chronically implantable medical electrical leads.

In the past, with the objective to further improve the mechanical properties of silicone insulation tubing, so that the thickness thereof may be reduced, we have investigated the incorporation reinforcing strands/fibers into the wall of silicone insulation tubing, for example, the Dow Corning ETR elastomer, Silastic® 4750, and the NuSil MED-4755, reinforced with either a Polyethylene Terephthalate (PET) polyester fiber or a polyether ether ketone (PEEK) fiber. However, our investigations showed that the inclusion of these types of reinforcing members caused an increase to the wall thickness of the silicone insulation tubing and, thus, to an overall diameter of the corresponding medical electrical lead beyond that which was desired. Such an increase in diameter is contrary to the continued demand for downsized diameters of implantable leads. Thus, there is a need to enhance the properties of silicone insulation for implantable medical electrical leads without increasing the wall thickness thereof, and to even also allow for a reduction in the wall thickness of the silicone insulation, without compromising the mechanical performance and abrasion resistance thereof, on which the integrity of electrical isolation for the resultant lead relies.

SUMMARY

The present invention provides improvements to silicone insulation for implantable medical electrical leads. The insulation includes a plurality of fibers embedded therein. The fibers may be ultra high molecular weight multi-filament fibers, for example fabricated of polyethylene. In some preferred embodiments, each fiber of the plurality includes approximately 25 monofilaments and has a titer of approximately 25. The plurality of fibers are embedded within a wall of the insulation that in some preferred embodiments preferably has a thickness of no greater than approximately 0.008 inch.

A first fiber of the plurality preferably extends helically, and a second fiber of the plurality preferably extends linearly such that the second crosses over or under and directly adjacent to the first at a plurality of points, which are spaced apart from one another along an overall length of the silicone insulation. The aforementioned wall thickness is maintained, since, at least at each crossing point of the first and second multi-filament fibers, a coincident cross-section of each of the fibers is compressed in the radial direction.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

DETAILED DESCRIPTION

The following detailed description is exemplary in nature and is not intended to limit the scope, applicability, or configuration of the embodiments. Rather, the following description provides practical illustrations for implementing exemplary embodiments of the present invention. Examples of constructions, materials, dimensions and manufacturing processes are provided for selected elements, and all other elements employ that which is known to those skilled in the field of the invention. Those skilled in the art will recognize that some of the examples may have suitable alternatives.

Figure 1A:
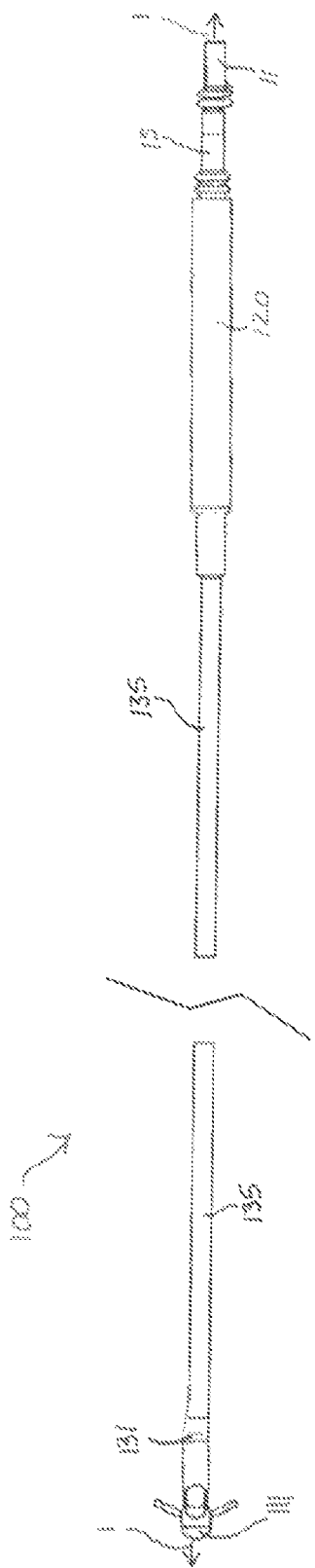
FIGS. 1A-B are a plan view and a section view of portions of an exemplary medical electrical lead that includes reinforced silicone insulation, according to some embodiments.
Figure 1B:
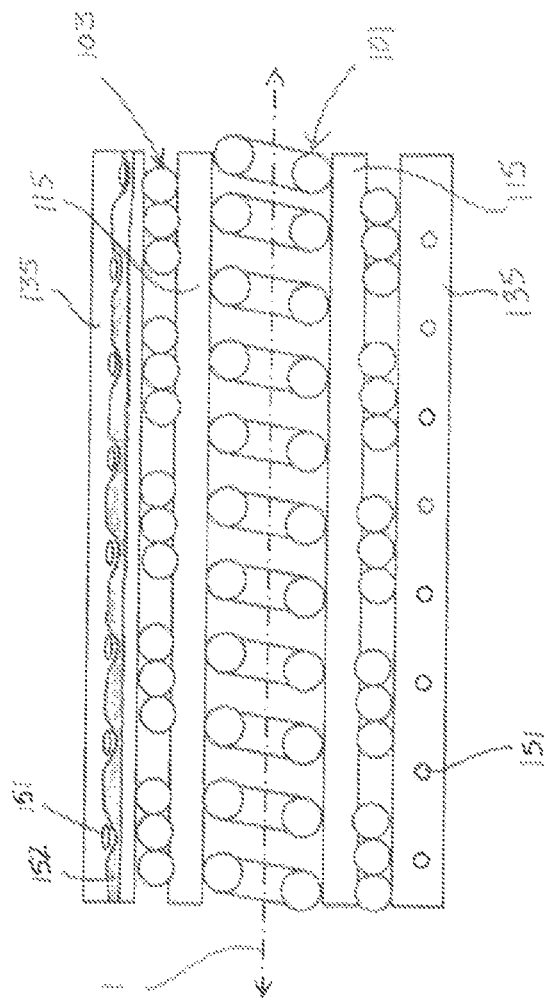

FIG. 1A is a plan view of an exemplary implantable medical electrical lead 100, which is configured for cardiac pacing and sensing. FIG. 1A illustrates lead 100 including a pin connector contact 11 and a ring connector contact 13, located at a proximal end of lead 100, and a ring electrode 131 and a tip electrode 111, located at a distal end of lead 100. FIG. 1B is a longitudinal cross-section view through a portion of lead 100 that is located between ring connector contact 13 and ring electrode 131, according to some embodiments, wherein an inner coiled conductor 101 and an outer coiled conductor 103 may be seen. Those skilled in the art will appreciate that inner conductor 101 extends along a length of lead 100 and electrically couples pin contact 11 to tip electrode 111, while outer conductor 103, which is electrically isolated from inner conductor 101 by an inner insulation layer 115, extending directly therebetween, electrically couples ring contact 13 to ring electrode 131. FIGS. 1A-B further illustrate lead 100 including an outer insulation layer 135 that extends directly around outer conductor 103 to isolate conductor 103 from an environment external to lead 100, that is, the implant environment, when lead 100 is implanted. According to the embodiment of FIG. 1A, an additional layer of insulating material, in the form of a connector sleeve 120, overlies outer insulation layer 135 in proximity to ring connector contact 13, for example, to provide strain relief.

As indicated above, a number of silicone elastomers are suitable for the primary insulation in implantable medical electrical leads, such as that provided by the illustrated inner and outer insulation layers 115, 135. In fact, in a number of applications, silicone elastomers are preferred over other insulating materials due to their proven history of chronic implant stability. In addition to the commercially available silicone elastomers referenced above, the Dow Corning® silicone elastomer known as MDX4-4516, as well as a high performance (HP) version thereof, have been employed as primary insulation in implantable medical electrical leads with specified minimum wall thicknesses. According to some standards, a specified minimum thickness of outer insulation formed by the MDX4-4516 silicone elastomer has ranged from approximately 0.012 inch to approximately 0.015 inch, and that of inner insulation, formed by the same, has been approximately 0.009 inch. For the above-mentioned NuSil MED-4719P silicone elastomer, some standards have specified approximately 0.010 inch for a minimum thickness of outer insulation, and approximately 0.005 inch for a minimum thickness of inner insulation. In view of the continued demand for downsized leads, we have investigated reinforced silicone insulation, with the objective of reducing insulation wall thicknesses without compromising the mechanical performance and abrasion resistance thereof, on which the integrity of electrical isolation for the resultant lead relies.

Figure 2:
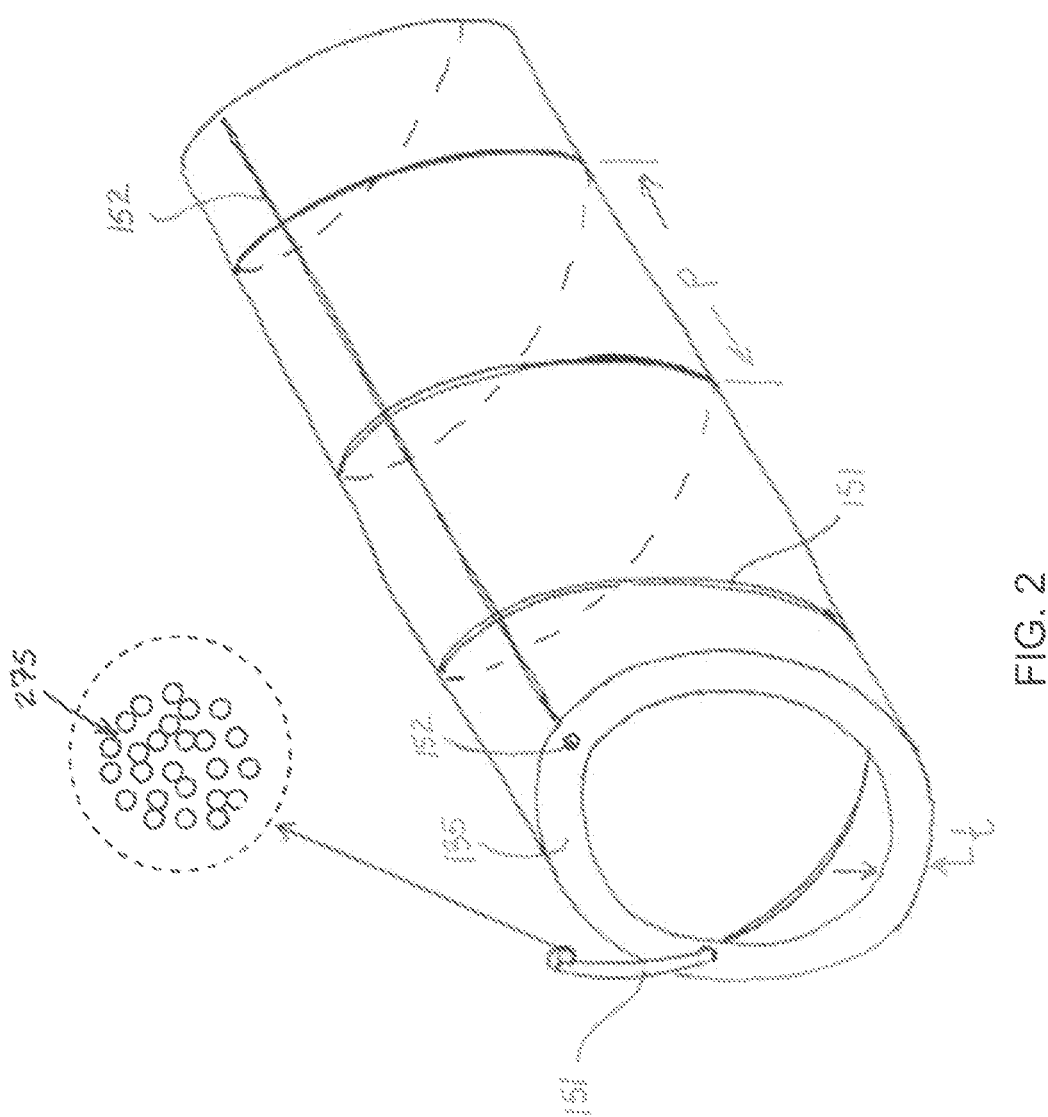
FIG. 2 is a perspective view of a portion of an implantable insulation member, according to some embodiments, wherein a segment of an embedded multi-filament fiber is shown protruding from an end of the insulation member and an enlarged detail view of an exemplary radial cross-section of the fiber is included.

With further reference to FIG. 1B, a first multi-filament fiber 151 and a second multi-filament fiber 152 are shown embedded in outer insulation layer 135. FIG. 2 is a perspective view of a portion of an implantable insulation member, for example, a tubing which forms outer insulation layer 135 of FIGS. 1A-B, according to some embodiments, wherein a segment of first embedded multi-filament fiber 151 is shown protruding from an end of the insulation member. FIGS. 1B and 2 illustrate first fiber 151 extending helically around a central longitudinal axis 1 of lead 100, and along the overall length of layer 135, at an approximately constant radial distance from central longitudinal axis 1, and second fiber 152 extending linearly along the overall length layer 135 at the same approximately constant radial distance from central longitudinal axis 1. Each of fibers 151, 152 may be formed from polymer materials such as: polyimide, PET, PEEK, Polyetherketoneketone (PEKK), Nylon, and liquid crystal polymer (LCP); however, according to preferred embodiments of the present disclosure, each of multi-filament fibers 151, 152 is ultra high molecular weight polyethylene (UHMWPE) being formed of approximately 25 monofilaments and having a titer of approximately 25 dtex. An enlarged detail view of an exemplary radial cross-section of fiber 151, in FIG. 2, illustrates a plurality of mono-filaments 275 that make up fiber 151.

With reference back to FIG. 1B, it may be appreciated that at least at the points where second fiber 152 crosses under and directly adjacent to first fiber 151, the coincident cross-section of each of the first and second embedded fibers is flattened, or compressed in the radial direction, such that the incorporation of such overlapping fibers need not cause an undue increase in a thickness t of layer 135. Furthermore, we expect that the cross-section of each of a plurality of UHMWPE multi-filament fibers, for example, fibers 151, 152, are flattened, or compressed, to some degree, along an entire embedded length thereof, for example, as the multi-filament fibers are unspooled and overlaid onto an initially extruded layer of silicone elastomer, for example, NuSil MED-4755, which is subsequently over-extruded with another layer of the same to embed the fibers in the wall of the insulation layer. According to an exemplary embodiment, thickness t of outer insulation layer 135 is no greater than 0.008 inch (being specified at 0.005 inch, minimum) and each of fibers 151, 152 is a Dyneema Purity® TG dtex 25 TS180 grade high performance polyethylene fiber (available from DSM of Heerlen (NL)). It is anticipated that the incorporation of a plurality of the preferred UHMWPE multi-filament fibers will reinforce the silicone insulation in order to improve insulation mechanical performance and abrasion resistance, at a given wall thickness, during chronic implant. Also, the inclusion of one or more linearly extending multi-filament fibers, for example, like second fiber 152, may enhance the extractability of a lead that includes the reinforced insulation, such as lead 100, from the chronic implant environment.

Figure 3:
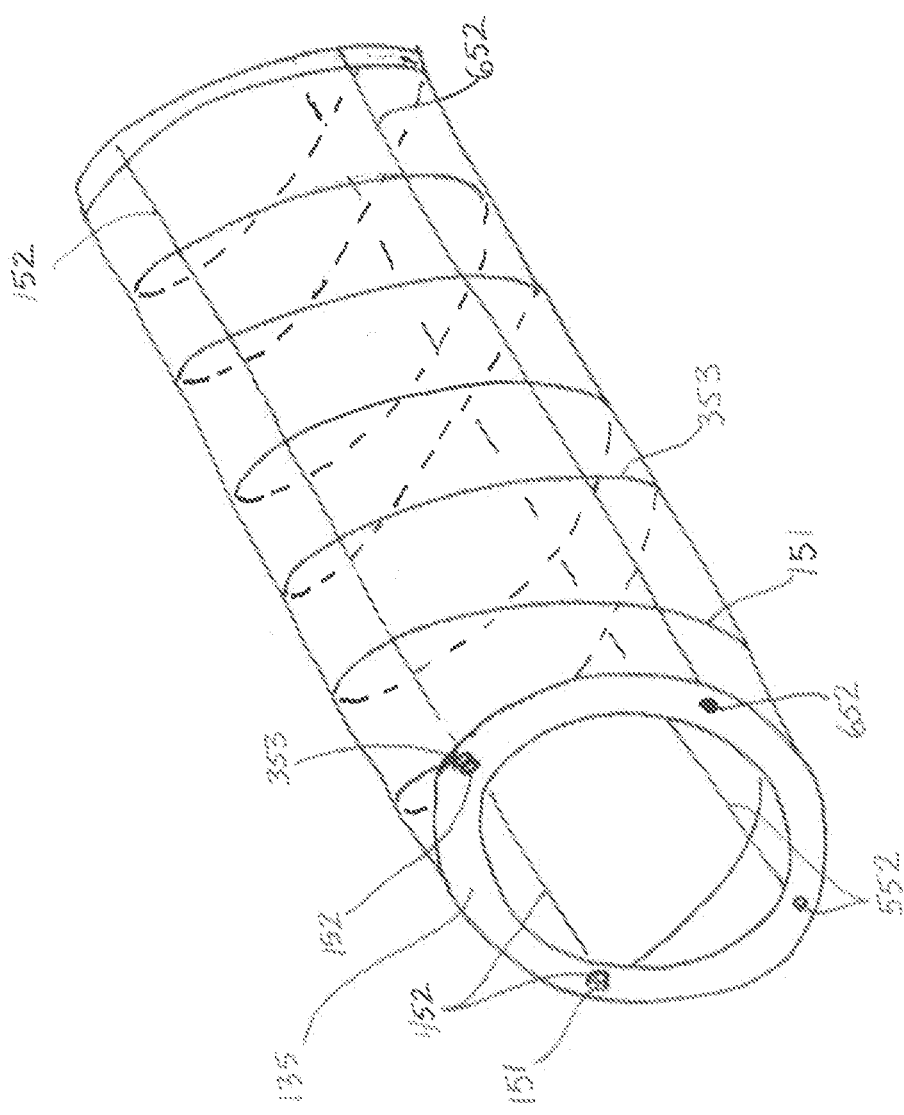
FIG. 3 is a perspective view of an alternative embodiment of the portion of the implantable insulation member.

FIG. 3 is a perspective view of an alternate embodiment of the tubing member that forms outer insulation layer 135. FIG. 3 illustrates a plurality of embedded UHMWPE multi-filament fibers including a third fiber 353, which extends helically, and fourth, fifth and sixth fibers 452, 552 and 652, each of which extend linearly, in addition to the above-described first and second fibers 151, 152. According to some preferred embodiments, all of fibers 151, 152, 353, 452, 552 and 652 extend at the same approximately constant radial distance from central longitudinal axis 1 (FIGS. 1A-B), along the overall length of layer 135. Like first and second fibers 151, 152, each of third, fourth, fifth and sixth multi-filament fibers 353, 452, 552, 652 is preferably UHMWPE being formed of approximately 25 monofilaments and having a titer of approximately 25 dtex, for example, being the aforementioned Dyneema Purity® fiber. With reference back to FIG. 2 a pitch P of the helical extension of first multi-filament fiber 151 may be between approximately 0.03 inch and approximately 0.1 inch, such that, with reference to FIG. 3, third fiber 353 may be offset, along the length of layer 135, from first multi-filament fiber 151 by approximately one half of pitch P. FIG. 3 further illustrates each of linearly extending fibers 152, 452, 552 and 652 being circumferentially offset from one another such that second fiber 152 extends opposite fifth fiber 552 and fourth fiber 452 extends opposite sixth fiber 652.

As may be seen, at the end of layer 135, in FIG. 3, where first fiber 151 is coincident with fourth fiber 454 and where second fiber 152 is coincident with third fiber 353, the cross-section of each of the multi-filament fibers flattens, or radially compresses at least at the points where one fiber crosses over, or under, another fiber, as was previously described in conjunction with FIGS. 1B and 2, so that the plurality of multi-filament fibers need not cause an undue increase in thickness t of layer 135. It should be understood that additional embodiments may include additional numbers of embedded UHMWPE multi-filament fibers, for example, additional helically extending fibers offset linearly from one another and/or additional linearly extending fibers circumferentially offset from one another, and that the additional fibers need not impact thickness t. Thus, it is anticipated that, along an overall length of outer insulation layer 135, both long term stability, for providing electrical isolation within a chronic implant environment, and a maximum wall thickness t of approximately 0.008 inch may be maintained, when any number of the preferred UHMWPE multi-filament fibers, arranged according to the pattern illustrated in FIGS. 2 and 3, are embedded therein, and that the embedded fibers, in particular any or all of linearly extending fibers 152, 452, 552, 652, may further enhance the extractability of a lead which includes the reinforced insulation, such as lead 100, from the chronic implant environment.

In the foregoing detailed description, the invention has been described with reference to specific embodiments. However, it may be appreciated that various modifications and changes can be made without departing from the scope of the invention as set forth in the appended claims. For example, with reference to FIG. 1B, inner insulation layer 115 may be reinforced with the plurality of HMWPE multi-filament fibers according to any of the described embodiments. Furthermore it is contemplated that the above-described arrangements of the plurality of HMWPE multi-filament fibers can be similarly embedded within alternate configurations of silicone insulation for implantable medical electrical leads, for example, insulation extruded in the form of multi-lumen tubing.

The invention claimed is:

1. An implantable medical electrical lead that includes a central longitudinal axis, an elongate conductor, an electrode coupled to the conductor and a layer of silicone insulation extending directly around, and along a length of the elongate conductor to electrically isolate the conductor, the layer of silicone having an overall length, an outer surface and a thickness, between the outer surface and the conductor, of no more than approximately 0.008 inch, wherein the lead comprises:
   a plurality of ultra high molecular weight polyethylene multi-filament fibers, the plurality comprising a first fiber and a second fiber, each of the plurality of fibers being embedded in the layer of silicone insulation, between the outer surface and the conductor, and each of the plurality of fibers including approximately 25 monofilaments and having a titer of approximately 25 dtex; and
   wherein the first multi-filament fiber extends helically around the central longitudinal axis of the lead and along the overall length of the layer of silicone insulation at an approximately constant radial distance from the central longitudinal axis;
   the second multi-filament fiber extends linearly along the overall length of the layer of silicone insulation at the same approximately constant radial distance from the central longitudinal axis, such that the second fiber crosses over or under and directly adjacent to the first fiber at a plurality of points, which are spaced apart from one another along the overall length of the layer of silicone insulation; and
   at each crossing point of the first and second multi-filament fibers, a coincident cross-section of each of the first and second fibers is compressed in a radial direction.

2. The lead of claim 1, wherein the outer surface of the layer of silicone insulation is exposed to an environment external to the lead.

3. The lead of claim 1, wherein a pitch of the helical extension of the first multi-filament fiber is between approximately 0.03 inch and approximately 0.1 inch.

4. The lead of claim 3, wherein:
   the plurality multi-filament fibers further comprises a third fiber, the third multi-filament fiber extending helically around the central longitudinal axis of the lead and along the overall length of the layer of silicone insulation, at the same approximately constant radial distance, and being offset, along the overall length, from the first multi-filament fiber by approximately one half of the pitch;
   the second multi-filament fiber crosses over or under and directly adjacent to the third fiber at a second plurality of points, which are spaced apart from one another along the overall length of the layer of silicone insulation; and
   at each crossing of the second and third multi-filament fibers, a coincident cross-section of each of the second and third fibers is compressed in the radial direction.

5. The lead of claim 4, wherein:
   the plurality of multi-filament fibers further comprises a fourth fiber, the fourth multi-filament fiber extending linearly along the overall length of the layer of silicone insulation, at the same approximately constant radial distance, and being offset from the second multi-filament fiber, circumferentially, about the central longitudinal axis of the lead;
   the fourth multi-filament fiber crosses over or under and directly adjacent to each of the first and third fibers at a third and fourth plurality of points, respectively, which are each spaced apart from one another along the overall length of the layer of silicone insulation; and
   at each crossing of the fourth fiber and the first fiber and of the fourth fiber and the third fiber, a coincident cross-section of each of the fourth, first and third fibers is compressed in the radial direction.

6. The lead of claim 5, wherein:
   the plurality of multi-filament fibers further comprises a fifth fiber and sixth fiber, the fifth and sixth multi-filament fibers extending linearly along the overall length of the layer of silicone insulation, at the same approximately constant radial distance, each of the fifth and sixth fibers being offset from one another and from each of the second and fourth fibers, circumferentially, about the central longitudinal axis of the lead;
   the fourth multi-filament fiber extends opposite the second multi-filament fiber;
   the sixth multi-filament fiber extends opposite the fifth multifilament fiber;
   the fifth multi-filament fiber crosses over or under and directly adjacent to each of the first and third fibers at a fifth and sixth plurality of points, respectively, which are each spaced apart from one another along the overall length of the layer of silicone insulation;
   at each crossing of the fifth fiber and the first fiber and of the fifth fiber and the third fiber, a coincident cross-section of each of the fifth, first and third fibers is compressed in the radial direction;
   the sixth multi-filament fiber crosses over or under and directly adjacent to each of the first and third fibers at a seventh and eighth plurality of points, respectively, which are each spaced apart from one another along the overall length of the layer of silicone insulation; and
   at each crossing of the sixth fiber and the first fiber and of the sixth fiber and the third fiber, a coincident cross-section of each of the sixth, first and third fibers is compressed in the radial direction.

7. The lead of claim 1, wherein:
   the plurality of multi-filament fibers further comprises a third fiber, the third multi-filament fiber extending linearly along the overall length of the layer of silicone insulation, at the same approximately constant radial distance, and being offset from the second multi-filament fiber, circumferentially, about the central longitudinal axis of the lead;
   the third multi-filament fiber crosses over or under and directly adjacent to the first fiber at a second plurality of points, which are spaced apart from one another along the overall length of the layer of silicone insulation; and at each crossing of the first and third multi-filament fibers, a coincident cross-section of each of the first and third fibers is compressed in the radial direction.

8. The lead of claim 7, wherein:
the plurality of multi-filament fibers further comprises a fourth fiber and a fifth fiber, the fourth and fifth multi-filament fibers extending linearly along the overall length of the layer of silicone insulation, at the same approximately constant radial distance, each of the fourth and fifth fibers being offset from one another and from each of the second and third fibers, circumferentially, about the central longitudinal axis of the lead;
the third multi-filament fiber extends opposite the second multi-filament fiber;
the fifth multi-filament fiber extends opposite the fourth multifilament fiber;
the fifth multi-filament fiber crosses over or under and directly adjacent to the first fiber at a third plurality of points, which are each spaced apart from one another along the overall length of the layer of silicone insulation;
at each crossing of the fifth fiber and the first fiber, a coincident cross-section of each of the fifth and first fibers is compressed in the radial direction;
the sixth multi-filament fiber crosses over or under and directly adjacent to the first fiber at a fourth plurality of points, which are each spaced apart from one another along the overall length of the layer of silicone insulation; and
at each crossing of the sixth fiber and the first fiber, a coincident cross-section of each of the sixth and first fibers is compressed in the radial direction.

9. An implantable insulation member including an overall length, an outer surface, an inner surface forming a lumen, to receive a conductor of an implantable medical electrical lead, a central longitudinal axis and an extruded wall of silicone that extends along the overall length, defines the outer surface and the inner surface of the insulation member, and has a thickness of no greater than approximately 0.008 inch between the inner surface and the outer surface, wherein the insulation member comprises:
a plurality of ultra high molecular weight polyethylene multi-filament fibers, the plurality of fibers comprising a first fiber and a second fiber, each of the plurality of fibers being embedded in the extruded wall of silicone, between the outer surface and the inner surface of the insulation member, and each of the plurality including approximately 25 monofilaments and having a titer of approximately 25 dtex; and
wherein the first multi-filament fiber extends helically around the central longitudinal axis of the insulation member and along the overall length of the insulation member at an approximately constant radial distance from the central longitudinal axis;
the second multi-filament fiber extends linearly along the overall length of the insulation member at the same approximately constant radial distance from the central longitudinal axis, such that the second fiber crosses over or under and directly adjacent to the first fiber at a plurality of points, which are spaced apart from one another along the overall length of the insulation member; and
at each crossing of the first and second multi-filament fibers, a coincident cross-section of each of the first and second fibers is compressed in a radial direction.

10. The insulation member of claim 9, wherein a pitch of the helical extension of the first multi-filament fiber is between approximately 0.03 inch and approximately 0.1 inch.

11. The insulation member of claim 10, wherein:
the plurality multi-filament fibers further comprises a third fiber, the third multi-filament fiber extending helically around the central longitudinal axis of the insulation member and along the overall length of the insulation member, at the same approximately constant radial distance, and being offset, along the overall length, from the first multi-filament fiber by approximately one half of the pitch;
the second multi-filament fiber crosses over or under and directly adjacent to the third fiber at a second plurality of points, which are spaced apart from one another along the overall length of the insulation member; and
at each crossing of the second and third multi-filament fibers, a coincident cross-section of each of the second and third fibers is compressed in the radial direction.

12. The insulation member of claim 11, wherein:
the plurality of multi-filament fibers further comprises a fourth fiber, the fourth multi-filament fiber extending linearly along the overall length of the insulation member, at the same approximately constant radial distance, and being offset from the second multi-filament fiber, circumferentially, about the central longitudinal axis of the insulation member;
the fourth multi-filament fiber crosses over or under and directly adjacent to each of the first and third fibers at a third and fourth plurality of points, respectively, which are each spaced apart from one another along the overall length of the insulation member; and
at each crossing of the fourth fiber and the first fiber and of the fourth fiber and the third fiber, a coincident cross-section of each of the fourth, first and third fibers is compressed in the radial direction.

13. The insulation member of claim 12, wherein:
the plurality of multi-filament fibers further comprises a fifth fiber and sixth fiber, the fifth and sixth multi-filament fibers extending linearly along the overall length of the insulation member, at the same approximately constant radial distance, each of the fifth and sixth fibers being offset from one another and from each of the second and fourth fibers, circumferentially, about the central longitudinal axis of the insulation member;
the fourth multi-filament fiber extends opposite the second multi-filament fiber;
the sixth multi-filament fiber extends opposite the fifth multifilament fiber;
the fifth multi-filament fiber crosses over or under and directly adjacent to each of the first and third fibers at a fifth and sixth plurality of points, respectively, which are each spaced apart from one another along the overall length of the insulation member;
at each crossing of the fifth fiber and the first fiber and of the fifth fiber and the third fiber, a coincident cross-section of each of the fifth, first and third fibers is compressed in the radial direction;
the sixth multi-filament fiber crosses over or under and directly adjacent to each of the first and third fibers at a seventh and eighth plurality of points, respectively, which are each spaced apart from one another along the overall length of the insulation member; and
at each crossing of the sixth fiber and the first fiber and of the sixth fiber and the third fiber, a coincident cross-section of each of the sixth, first and third fibers is compressed in the radial direction.

14. The insulation member of claim 9, wherein:
the plurality of multi-filament fibers further comprises a third fiber, the third multi-filament fiber extending linearly along the overall length of the insulation member, at the same approximately constant radial distance, and being offset from the second multi-filament fiber, circumferentially, about the longitudinal axis of the insulation member;
the third multi-filament fiber crosses over or under and directly adjacent to the first fiber at a second plurality of points, which are spaced apart from one another along the overall length of the insulation member; and
at each crossing of the first and third multi-filament fibers, a coincident cross-section of each of the first and third fibers is compressed in the radial direction.

15. The insulation member of claim 14, wherein:
the plurality of multi-filament fibers further comprises a fourth fiber and a fifth fiber, the fourth and fifth multi-filament fibers extending linearly along the overall length of the insulation member, at the same approximately constant radial distance, each of the fourth and fifth fibers being offset from one another and from each of the second and third fibers, circumferentially, about the longitudinal axis of the insulation member;
the third multi-filament fiber extends opposite the second multi-filament fiber;
the fifth multi-filament fiber extends opposite the fourth multifilament fiber;
the fifth multi-filament fiber crosses over or under and directly adjacent to the first fiber at a third plurality of points, which are each spaced apart from one another along the overall length of the insulation member;
at each crossing of the fifth fiber and the first fiber, a coincident cross-section of each of the fifth and first fibers is compressed in the radial direction;
the sixth multi-filament fiber crosses over or under and directly adjacent to the first fiber at a fourth plurality of points, which are each spaced apart from one another along the overall length of the insulation member; and
at each crossing of the sixth fiber and the first fiber, a coincident cross-section of each of the sixth and first fibers is compressed in the radial direction.

16. An implantable medical electrical lead that includes a central longitudinal axis, an elongate conductor, an electrode coupled to the conductor and a layer of silicone insulation extending directly around, and along a length of the elongate conductor to electrically isolate the conductor, the layer of silicone having an overall length, an outer surface and a thickness, between the outer surface and the conductor, of no more than approximately 0.008 inch, wherein the lead comprises:
a plurality of ultra high molecular weight polyethylene multi-filament fibers, the plurality comprising a first fiber and a second fiber, each of the plurality of fibers being embedded in the layer of silicone insulation, between the outer surface and the conductor; and
wherein the first multi-filament fiber extends helically around the central longitudinal axis of the lead and along the overall length of the layer of silicone insulation at an approximately constant radial distance from the central longitudinal axis;
the second multi-filament fiber extends linearly along the overall length of the layer of silicone insulation at the same approximately constant radial distance from the central longitudinal axis, such that the second fiber crosses over or under and directly adjacent to the first fiber at a plurality of points, which are spaced apart from one another along the overall length of the layer of silicone insulation; and
at each crossing point of the first and second multi-filament fibers, a coincident cross-section of each of the first and second fibers is compressed in a radial direction.

17. An implantable medical electrical lead that includes a central longitudinal axis, an elongate conductor, an electrode coupled to the conductor and a layer of silicone insulation extending directly around, and along a length of the elongate conductor to electrically isolate the conductor, the layer of silicone having an overall length, an outer surface and a thickness, between the outer surface and the conductor, of no more than approximately 0.008 inch, wherein the lead comprises:
a plurality of ultra high molecular weight polyethylene multi-filament fibers, the plurality comprising a first fiber and a second fiber, each of the plurality of fibers being embedded in the layer of silicone insulation, between the outer surface and the conductor; and
wherein the first multi-filament fiber extends along the overall length of the layer of silicone insulation at an approximately constant radial distance from the central longitudinal axis;
the second multi-filament fiber extends linearly along the overall length of the layer of silicone insulation at the same approximately constant radial distance from the central longitudinal axis, such that the second fiber crosses over or under and directly adjacent to the first fiber at a plurality of points, which are spaced apart from one another along the overall length of the layer of silicone insulation; and
at each crossing point of the first and second multi-filament fibers, a coincident cross-section of each of the first and second fibers is compressed in a radial direction.

18. An implantable medical electrical lead that includes a central longitudinal axis, an elongate conductor, an electrode coupled to the conductor and a layer of silicone insulation extending directly around, and along a length of the elongate conductor to electrically isolate the conductor, the layer of silicone having an overall length, an outer surface and a thickness between the outer surface and the conductor, wherein the lead comprises:
a plurality of ultra high molecular weight polyethylene multi-filament fibers, the plurality comprising a first fiber and a second fiber, each of the plurality of fibers being embedded in the layer of silicone insulation, between the outer surface and the conductor; and
wherein the first multi-filament fiber extends along the overall length of the layer of silicone insulation at an approximately constant radial distance from the central longitudinal axis;
the second multi-filament fiber extends linearly along the overall length of the layer of silicone insulation at the same approximately constant radial distance from the central longitudinal axis, such that the second fiber crosses over or under and directly adjacent to the first fiber at a plurality of points, which are spaced apart from one another along the overall length of the layer of silicone insulation; and
at each crossing point of the first and second multi-filament fibers, a coincident cross-section of each of the first and second fibers is compressed in a radial direction.

* * * * *

UNITED STATES PATENT AND TRADEMARK OFFICE
CERTIFICATE OF CORRECTION

PATENT NO.           : 8,515,556 B2                              Page 1 of 1
APPLICATION NO.      : 12/915854
DATED                : August 20, 2013
INVENTOR(S)          : Richard D. Ries and James M. Olsen It is certified that error appears in the above-identified patent and that said Letters Patent is hereby corrected as shown below:

In the Claims:

Col. 6, line 37, delete "fifth multifilament fiber" and insert in place thereof -- fifth multi-filament fiber --;

Col. 7, line 17, delete "fourth multifilament fiber" and insert in place thereof -- fourth multi-filament fiber --;

Col. 8, line 51, delete "fifth multifilament fiber" and insert in place thereof -- fifth multi-filament fiber --.

Signed and Sealed this
Second Day of September, 2014

Michelle K. Lee
*Deputy Director of the United States Patent and Trademark Office*